(12) United States Patent
Nishimura et al.

(10) Patent No.: US 6,666,956 B1
(45) Date of Patent: Dec. 23, 2003

(54) METHOD FOR DISTILLING POLYMERIZABLE COMPOUND OR LIQUID CONTAINING POLYMERIZABLE COMPOUND

(75) Inventors: Takeshi Nishimura, Himeji (JP); Yukihiro Matsumoto, Kobe (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/506,715

(22) Filed: Feb. 18, 2000

(30) Foreign Application Priority Data

Feb. 18, 1999 (JP) .......................................... 11-040275

(51) Int. Cl.[7] .............................. B01D 3/32; B01D 3/42; C07C 51/44
(52) U.S. Cl. ............................. 203/1; 203/99; 203/100; 203/DIG. 21; 562/600; 159/27.1; 159/44; 159/47.1
(58) Field of Search ....................... 203/8, 99, DIG. 21, 203/DIG. 25, 98, 1, 100; 562/600; 159/27.1, 44, 47.1

(56) References Cited

U.S. PATENT DOCUMENTS

| | | | |
|---|---|---|---|
| 3,177,129 A | * | 4/1965 | Hackins, Jr. ................ 202/153 |
| 3,280,010 A | * | 10/1966 | Creighton et al. ............ 203/95 |
| 4,019,866 A | | 4/1977 | Jaswal et al. ................ 23/260 |
| 4,490,215 A | * | 12/1984 | Bannon ........................ 203/98 |
| 4,661,207 A | | 4/1987 | Kurtz .......................... 203/3 |
| 5,897,749 A | | 4/1999 | Kroker et al. ................. 203/2 |
| 6,294,056 B1 | * | 9/2001 | Matsumoto et al. .......... 203/90 |
| 6,348,135 B1 | * | 2/2002 | Nakahara et al. ............. 203/8 |

FOREIGN PATENT DOCUMENTS

| | | |
|---|---|---|
| EP | 1043050 | * 10/2000 |
| GB | 1 265 738 | 3/1972 |

OTHER PUBLICATIONS

Kisten, "Distillation Operation", McGraw–Hill Publishing Co. p. 84.*
European Search Report.
G.C. Shah, Troubleshooting Distillation Columns, *Chemical Engineering*, Jul. 31, 1978, pp 70–78.

* cited by examiner

Primary Examiner—Virginia Manoharan
(74) Attorney, Agent, or Firm—Edwards & Angell, LLP; David G. Conlin; Lisa Swiszcz Hazzard

(57) ABSTRACT

In distillation of a polymerizable compound such as (meth) acrylic acid or a liquid containing such a polymerizable compound with use of a distillation column equipped with a reboiler, (a) a vertical multi-tube reboiler whose outlet nozzle inside diameter (D1) is 0.2 to 1 time its reboiler shell inside diameter (D2) is used as the reboiler, (b) an outlet of an outlet nozzle of the reboiler to a gas-phase section of the distillation column is provided at a position such that a distance L from the top tubesheet of the reboiler to the lower end of the outlet of the outlet nozzle satisfies $L=(0.4$ to $3)\times D1$, and (c) a liquid level in the distillation column is maintained in a range such that a height H of the liquid level from the top tubesheet of the reboiler satisfies $H=(0.1$ to $0.8)\times L$.

4 Claims, 6 Drawing Sheets

METHOD FOR DISTILLING POLYMERIZABLE COMPOUND OR LIQUID CONTAINING POLYMERIZABLE COMPOUND

FIELD OF THE INVENTION

The present invention relates to a method for distilling a polymerizable compound or a liquid containing a polymerizable compound, and more particularly relates to a method for distilling a polymerizable compound such as (meth) acrylic acid or a liquid containing such a polymerizable compound with use of a distillation column equipped with a reboiler through a distillation process that is kept stable for a long period of time by effectively preventing formation of a polymer in reboiler tubes, and hence, fouling of the tubes.

BACKGROUND OF THE INVENTION

Conventionally, distillation and purification of a polymerizable compound such as (meth)acrylic acid or a liquid containing such a polymerizable compound with use of a distillation device equipped with a multi-tube reboiler that is composed of a plurality of reboiler tubes fixed to tube sheets disposed inside the reboiler shell is widely practiced in industry.

Conventionally, a distillation device equipped externally with a multi-tube reboiler of a forced circulation type is widely used, as the foregoing distillation column equipped with the multi-tube reboiler. This distillation column is designed so that a pump disposed at a bottom of the distillation column is actuated with electric power or the like to pump up a liquid to be distilled (liquid to be processed, hereinafter referred to as process liquid) from the column bottom of the distillation column via the pump so as to forcibly circulate through the multi-tube reboiler.

To obtain a necessary ability, such a forced-circulation-type multi-tube reboiler sometimes requires circulation of a greater quantity of the liquid, a greater pass number, and the like.

The liquid supplied from the distillation column to the reboiler has been heated to a boiling point, and it partly evaporates due to pressure drop occurring when passing through the reboiler tubes. Therefore, distillation using the forced-circulation-type multi-tube reboiler undergoes a high ratio of evaporation of a liquid, thereby causing a polymerizable compound to easily polymerize. Accordingly, in distillation by using such a forced-circulation-type multi-tube reboiler, a polymer of a polymerizable compound tends to be formed thereby fouling surfaces of tubes, and hence, causing a problem of plugging.

A well-known scheme to cope with the foregoing problem is a scheme in which a valve or the like is provided at an outlet nozzle of a multi-tube reboiler (a tube connecting a reboiler shell of the multi-tube reboiler and a distillation column) so as to make a temperature inside the reboiler tubes of the multi-tube reboiler not higher than a boiling point. This scheme, however, does not completely solve the foregoing problem, due to the following drawbacks: channeling; a lower fluid velocity in a chamber; and a longer retention time. In case a polymer is formed and fouls tubes, the operation is suspended and the polymer is manually or chemically removed.

Furthermore, recently, from the viewpoint of energy saving, distillation is practiced by using a distillation column equipped with a multi-tube reboiler 52 of a natural circulation (thermosiphon) type shown in FIG. 6 that does not need electricity as power.

In the foregoing distillation in which a distillation column equipped with a natural-circulation-type multi-tube reboiler 52 is used, a liquid supplied to the multi-tube reboiler 52 from the distillation column 51 is heated in the multi-tube reboiler 52 thereby partially vaporizes. This causes density inside the distillation column 51 to become different from that inside the multi-tube reboiler 52, and hence, causes the process liquid to naturally circulate from the column bottom of the distillation column 51 to the multi-tube reboiler 52 with a lower density.

The distillation in which the natural-circulation-type multi-tube reboiler 52 is used is discussed by, for example, "Troubleshooting distillation columns" Chemical Engineering, Jul. 31, 1978, pp. 70–78. In this, a liquid level 57 in the distillation column 51 is considered from the viewpoint of efficiency of heat transfer in the distillation system.

As described in the foregoing reference, in the case where distillation is carried out with use of the distillation column 51 equipped with the natural-circulation-type multi-tube reboiler 52, the liquid level 57 in the distillation column 51 is maintained near the top tubesheet 53 of the multi-tube reboiler 52.

This is because, in the case where distillation is carried out with use of the distillation column 51 equipped with the natural-circulation-type multi-tube reboiler 52, the following problems are deemed to occur if the liquid level 57 in the distillation column 51 is set higher or lower than the top tubesheet 53 of the multi-tube reboiler 52 to which reboiler tubes 56 are fixed.

Namely, when the liquid level 57 in the distillation column 51 is lower than the top tubesheet 53, vaporization tends to increase, making the natural circulation difficult or impossible.

On the other hand, when the liquid level 57 in the distillation column 51 is higher than the top tubesheet 53, a heat transfer coefficient lowers, and further, in some cases, the reboiler outlet nozzle 54 becomes flooded with the liquid, and hydraulic hammer occurs.

Therefore, considering the heat transfer coefficient, in the case where distillation is carried out with use of the distillation column 51 equipped with the natural-circulation-type multi-tube reboiler 52, to avoid setting the liquid level 57 in the distillation column 51 higher or lower than the top tubesheet 53 of the multi-tube reboiler 52 is deemed preferable.

However, in the case where a polymerizable compound or a liquid containing a polymerizable compound is distilled with use of the above-described distillation column 51 equipped with the natural-circulation-type multi-tube reboiler 52, formation of a polymer in the reboiler tubes 56 cannot be avoided even in the case where distillation is carried out in a state in which the liquid level 57 in the distillation column 51 is maintained substantially as high as the top tubesheet 53 in the multi-tube reboiler 52. Therefore, as described above, when the tubes are fouled, the operation has to be stopped so that the polymer is removed manually or chemically.

SUMMARY OF THE INVENTION

An object of the present invention is to provide a method for distilling a polymerizable compound such as (meth) acrylic acid or a liquid containing such a polymerizable compound by using a distillation column equipped with a reboiler, by which method the distillation can be stably carried out for a long time of period by preventing formation of a polymer in reboiler tubes.

The inventors of the present invention made eager studies to achieve the above-described object, and discovered that the foregoing object could be achieved by maintaining a liquid level in the distillation column at a specific height by using a specific vertical multi-tube reboiler. Based on this finding, the inventors successfully completed the present invention.

More specifically, to achieve the foregoing object, a method for distilling a polymerizable compound or a liquid containing a polymerizable compound of the present invention is a method for distilling a polymerizable compound or a liquid containing a polymerizable compound by using a distillation column equipped with a reboiler, in which (a) as the reboiler, a vertical multi-tube reboiler whose outlet nozzle inside diameter (D1) is 0.2 to 1 time its reboiler shell inside diameter (D2) is used, (b) an outlet of an outlet nozzle of the reboiler to a gas-phase section of the distillation column is provided at a position satisfying:

$$L = (0.4 \text{ to } 3) \times D1$$

where L is a distance from a top tubesheet of the reboiler to a lower end of an outlet of the outlet nozzle, and D1 is the outlet nozzle inside diameter, and (c) a liquid level in the distillation column is maintained in a range satisfying:

$$H = (0.1 \text{ to } 0.8) \times L$$

where H is a height of the liquid level from the top tubesheet of the reboiler, L is a distance from the top tubesheet of the reboiler to the lower end of the outlet of the outlet nozzle, and D1 is the outlet nozzle inside diameter. By the foregoing method, a boiling point of the polymerizable compound or the polymerizable compound containing liquid in the reboiler is allowed to become higher than in conventional cases.

In other words, to achieve the foregoing object, in distillation of a polymerizable compound or a liquid containing a polymerizable compound by using a distillation column equipped with a vertical multi-tube reboiler, for suppression of polymerization of a polymerizable compound, an outlet of an outlet nozzle of the reboiler to a gas-phase section in the distillation column is provided at a position in accordance with an inside diameter (D1) of the outlet nozzle of the reboiler, and a height of a liquid level in the distillation column is maintained lower than a lower end of an outlet of the outlet nozzle and higher than a top tubesheet of the reboiler, so that a boiling point of the polymerizable compound or a liquid containing the polymerizable compound in the reboiler is raised.

With the foregoing arrangement, formation of a polymer in the reboiler tubes is effectively prevented, and distillation of a polymerizable compound or a liquid containing a polymerizable compound can be stably carried out for a long time of period.

For a fuller understanding of the nature and advantages of the invention, reference should be made to the ensuing detailed description taken in conjunction with the accompanying drawings.

DESCRIPTION OF THE PREFERRED EMBODIMENTS

Figure 1:
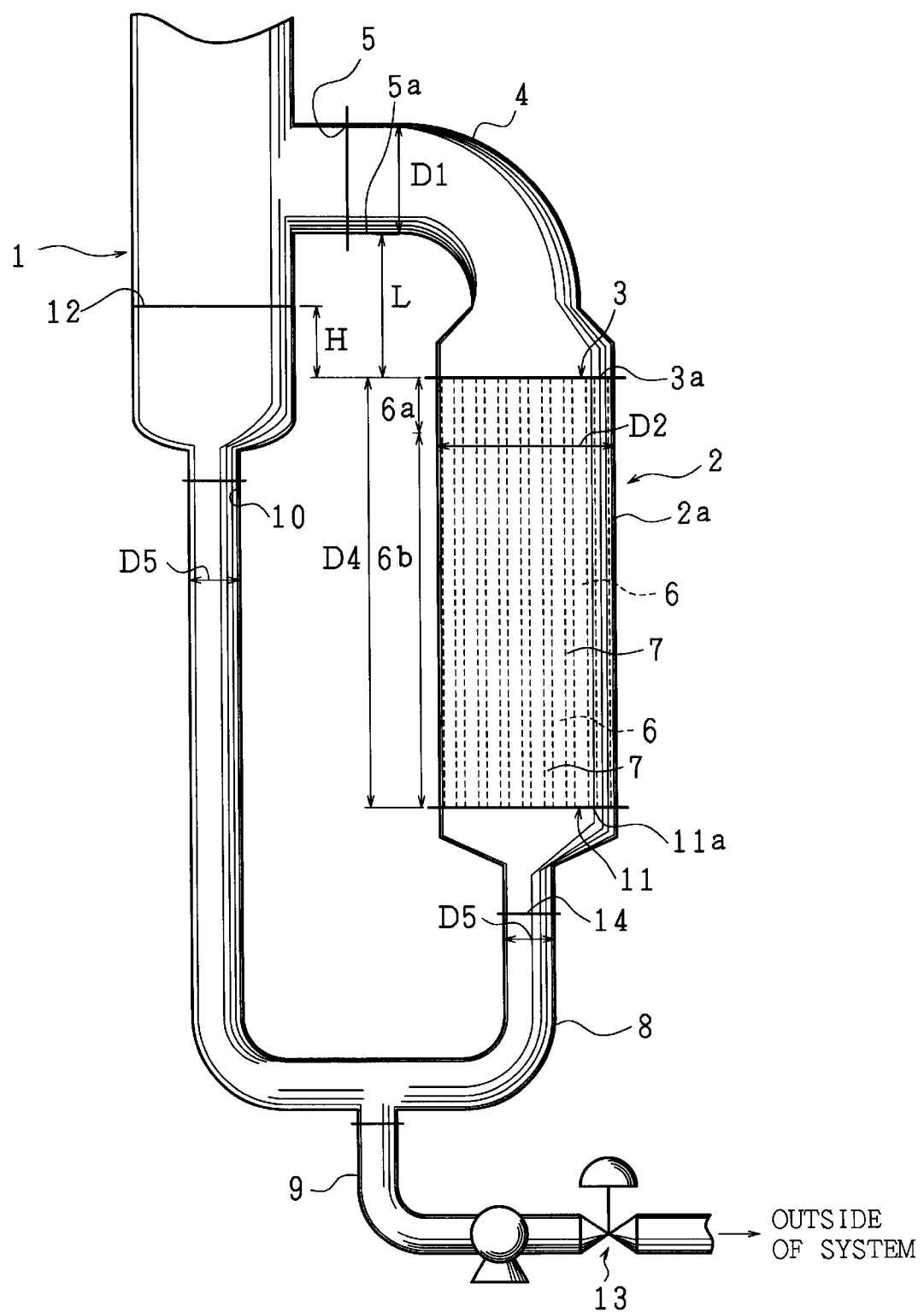
FIG. 1 is a view schematically illustrating an arrangement of a distillation device in accordance with an embodiment of the present invention.
Figure 2:
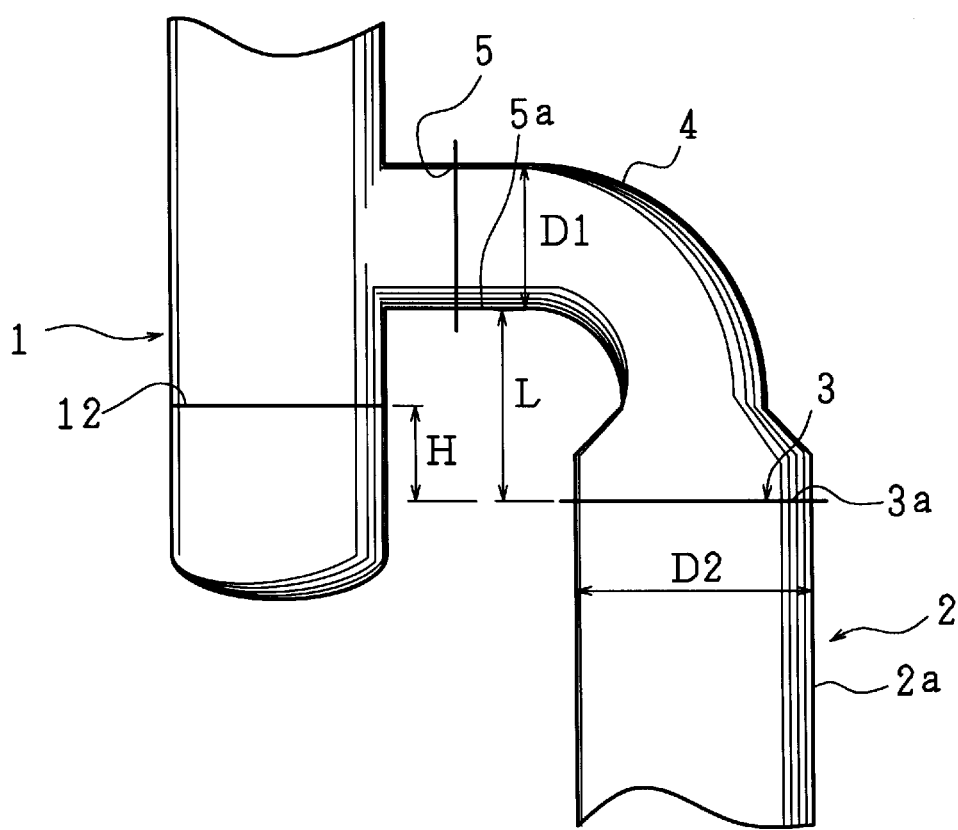
FIG. 2 is an enlarged view illustrating a principal part of the distillation device in accordance with the embodiment shown in FIG. 1.

The following description will explain an embodiment of the present invention, while referring to FIGS. 1 through 5. FIG. 1 is a view schematically illustrating a distillation device in accordance with an embodiment of the present invention, and FIG. 2 is an enlarged view illustrating a principal part of the distillation device in accordance with the embodiment shown in FIG. 1.

The distillation device adopted in the present invention is a distillation device equipped with a reboiler of a natural circulation type. The distillation device has a reboiler 2 outside a distillation column 1, as shown in FIGS. 1 and 2. The reboiler 2 is a heat source for heating a liquid at a column bottom for circulation of the same.

Used as the distillation column 1 is a distillation column including a gas-phase section therein, designed so that a low-boiling-point component is successively separated and moved to the gas-phase section. Besides, the distillation column 1 is connected with a liquid supply tube, not shown, which is to consecutively supply a liquid to be distilled to the distillation column 1.

The liquid to be distilled in the present invention, which is supplied to the distillation column 1 is either a polymerizable compound or a liquid containing a polymerizable compound. Herein, the polymerizable compound refers to any one of compounds having a property of becoming easily polymerized by heating. It is nor particularly limited, but typical examples thereof include organic compounds having vinyl groups. The liquid containing a polymerizable compound refers to any one of liquids containing polymerizable compounds, and types of other components thereof than the polymerizable compounds, for example, solvents, are not particularly limited.

Typical examples of a polymerizable compound of the present invention are (meth)acrylic acid and esters of the same. More specifically, they are, for example, methyl (meth)acrylate, ethyl (meth)acrylate, n-butyl (meth)acrylate, hydroxyethyl (meth)acrylate, hydroxypropyl (meth)acrylate, 2-ethylhexyl (meth)acrylate, and N,N-dimethylaminoethyl (meth)acrylate, though not particularly limited.

Figure 5:
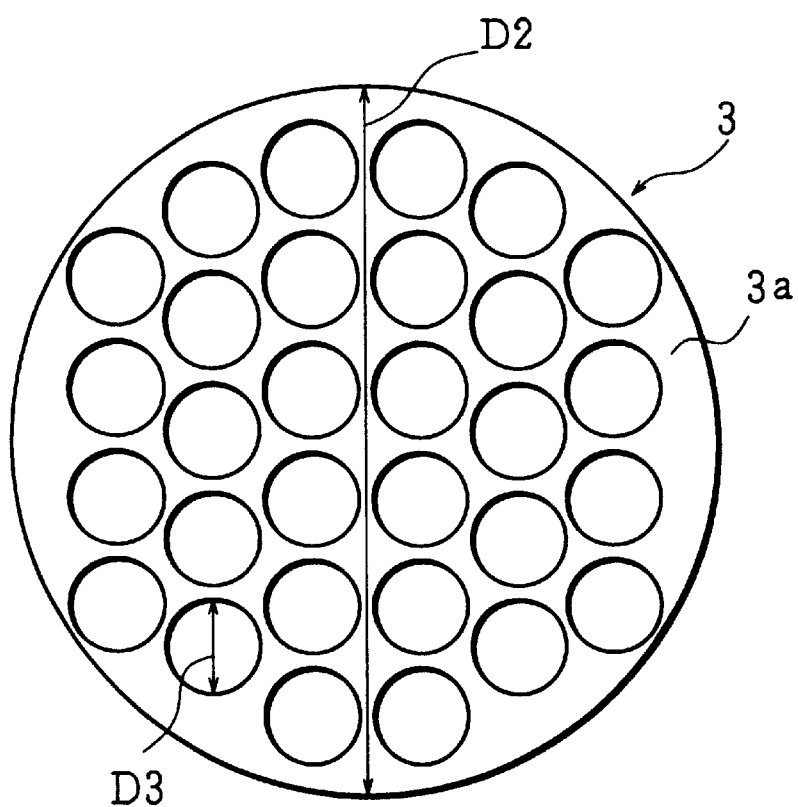
FIG. 5 is a plan view illustrating a top tubesheet to which reboiler tubes are fixed.
Figure 6:
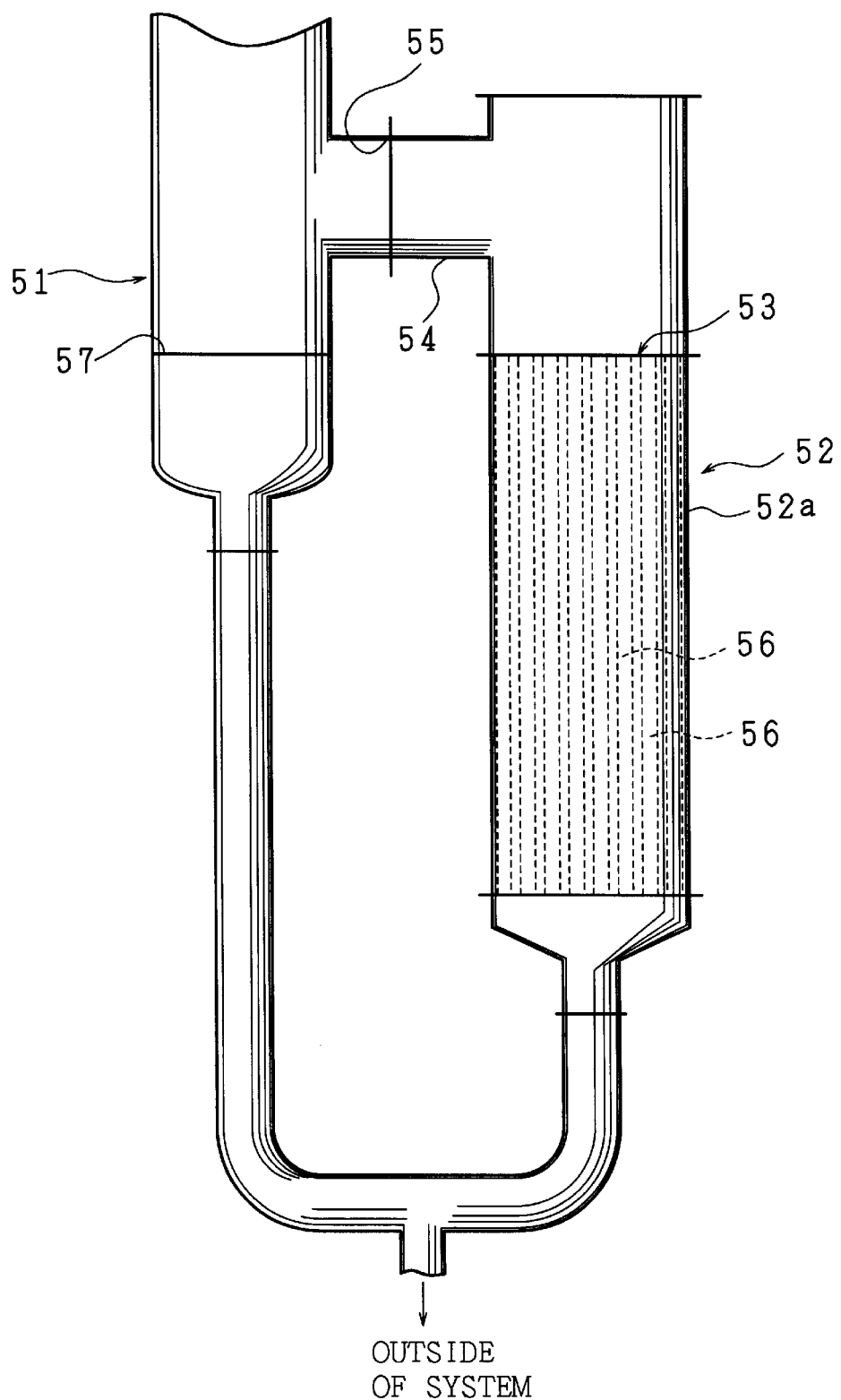
FIG. 6 is a view schematically illustrating an arrangement of a conventional distillation device equipped with a multi-tube reboiler.

Used as the foregoing reboiler 2 is a multi-tube reboiler as a so-called vertical multi-tube heat exchanger, in which, as shown in FIGS. 1 and 2, a process liquid, that is, a polymerizable compound or a liquid containing a polymerizable compound to be distilled, is caused to flow through reboiler tubes 6, while a heating medium 7 such as steam is caused to pass through a reboiler shell 2a, so that the process liquid flowing through the reboiler tubes 6 is heated via the reboiler tubes 6 fixed to tubesheets (top tubesheet 3 and bottom tubesheet 11) provided in the reboiler shell 2a. A plurality of the reboiler tubes 6 are fixed to the top tubesheet 3 and a bottom tubesheet 11 by welding or the like, as shown in FIG. 5.

As shown in FIG. 1, a reboiler lower end 14 is connected with a column bottom of the distillation column 1, via a conduit 8 as a tube connecting the reboiler 2 with the distillation column 1, which conduit 8 includes a liquid discharge piping 9. The liquid discharge piping 9 is branched out of the conduit 8 so that a part of the column bottom liquid is consecutively discharged as bottoms to outside the system by using a pump.

In other words, a high-boiling-point component is recovered in a liquid state from the column bottom of the distillation column 1 via the liquid discharge piping 9, while a low-boiling-point component is recovered in a vapor state from the column top of the distillation column 1. Incidentally, a joint part of the column bottom of the distillation column 1 with the conduit 8 and the liquid discharge piping 9 is omitted in FIG. 2, for simplification of the drawing.

Furthermore, as shown in FIGS. 1 and 2, the foregoing reboiler 2 is connected, at the top of the reboiler shell 2a, with the gas-phase section of the distillation column 1 via the reboiler outlet nozzle 4 as a tube for connecting the reboiler shell 2a with the distillation column 1.

With this, the process liquid supplied to the reboiler 2 through the conduit 8 from the column bottom of the distillation column 1 is heated in the reboiler 2. The process liquid thus heated goes up onto the top tubesheet 3 of the reboiler 2, and passes through the reboiler outlet nozzle 4, then goes to the gas-phase section of the distillation column 1 through an opening 5 as an outlet of the reboiler outlet nozzle 4 to the distillation column 1.

The opening 5 is designed to have an inside diameter equal to an inside diameter of the reboiler outlet nozzle 4 (D1: hereinafter referred to as outlet nozzle inside diameter). In other words, the outlet nozzle inside diameter (D1) of the present invention is equal to the inside diameter of the opening 5 as an outlet of the reboiler outlet nozzle 4 for connection thereof with the gas-phase section of the distillation column 1.

Adopted as the reboiler 2 in the present invention is a vertical multi-tube reboiler designed so that a ratio of the outlet nozzle inside diameter (D1), that is, an inside diameter of the opening 5, to the reboiler shell inside diameter (D2: hereinafter referred to as reboiler shell inside diameter), that is, D1/D2, is in a range of 0.2 to 1, or preferably, 0.3 to 1, or more preferably, 0.5 to 1.

In the case where the foregoing D1/D2 is less than 0.2, pressure loss increases, and vaporization occurs thereby causing formation of a polymer. On the other hand, in the case where the foregoing D1/D2 exceeds 1, channeling occurs and tends to cause a polymer to be formed where a fluid velocity is low. Thus, these cases are not preferable.

Incidentally, the reboiler shell inside diameter (D2) is not particularly limited, and can be set to any dimension as long as it can house a tube bundle. The outlet nozzle inside diameter (D1) and the reboiler shell inside diameter (D2) of the reboiler of the distillation device can be changed by replacing the reboiler outlet nozzle 4 and/or the reboiler shell 2a of the reboiler 2 connected with the distillation column 1.

Further, in the present invention, the reboiler outlet nozzle 4 is provided so that its opening 5 comes to a position higher than the top tubesheet 3 of the reboiler 2, depending on the outlet nozzle inside diameter (D1), that is, the inside diameter of the opening 5. More specifically, the reboiler outlet nozzle 4 is disposed at a position that satisfies the following relationship so as to be connected with the gas-phase section:

$$L=(0.4 \text{ to } 3) \times D1$$

or preferably, $$L=(0.7 \text{ to } 2.5) \times D1$$

or more preferably, $$L=(1 \text{ to } 2) \times D1$$

where L represents a distance from a top surface 3a of the top tubesheet 3 of the reboiler 2 to a lower end of the outlet of the reboiler outlet nozzle 4, that is, a lower inside end 5a of the opening 5, and D1 represents the outlet nozzle inside diameter.

L that is less than 0.4×D1 is not preferable since entrainment occurs. L that exceeds 3×D1 is not preferable, either, as the process liquid treated in the present invention is a polymerizable compound or a liquid containing a polymerizable compound that may cause not only an increase in pressure loss but also formation of a polymer.

Since carried out in the present invention is distillation of a polymerizable compound or a liquid containing a polymerizable compound, the distillation is preferably carried out by maintaining a height H of a liquid level 12 in the distillation column 1 from the top surface 3a of the top tubesheet 3 (hereinafter referred to as height of the liquid level 12, for conveniences' sake) in a range satisfying:

$$H=(0.1 \text{ to } 0.8) \times L$$

or preferably, $$H=(0.2 \text{ to } 0.7) \times L$$

or more preferably, $$H=(0.3 \text{ to } 0.5) \times L$$

where L represents the distance from the top surface 3a of the top tubesheet 3 of the reboiler 2 to the lower end of the outlet of the reboiler outlet nozzle 4, that is, the lower inside end 5a of the opening 5, and D1 represents the outlet nozzle inside diameter.

In the case where the height (H) of the liquid level 12 is maintained lower than 0.1×L, a polymer is formed, thereby fouling the reboiler tubes 6. This makes the operation of the distillation device unstable, or in some cases, impossible. On the other hand, in the case where the height (H) of the liquid level 12 is maintained higher than 0.8×L, flooding tends to occur, thereby making the operation unstable, or in some cases, impossible.

Preferably applicable as a technique for adjusting and maintaining the height (H) of the liquid level 12 at a position in the foregoing range is a technique in which a quantity of the bottoms discharged through the liquid discharge piping 9 is adjusted according to a quantity of the liquid supplied to the distillation column 1, so as to satisfy the foregoing relationship. This technique is preferable because it is simple and the adjustment is easy. The adjustment of the quantity of the discharged bottoms is carried out by using certain desirable adjustment means, for example, an control valve 13 fixed to the liquid discharge piping 9. To adjust the quantity of the discharged bottoms by the control valve 13, if a case in which the liquid level 12 is to be raised is taken as an example, an aperture of the valve 13 is closed so that a quantity of the liquid in the distillation column 1 increases, and then, when the liquid level 12 reaches to a predetermined desirable height, the quantity of the discharged bottoms through the liquid discharge piping 9 is set to a predetermined value. This enables to maintain the height (H) of the liquid level 12 in the aforementioned range.

Thus, in the present invention, it is possible to suppress polymerization of a polymerizable compound by setting and maintaining the position relationship between the liquid level 12 in the distillation column 1 and the top tubesheet 3 of the reboiler 2 so that the liquid level 12 in the distillation column 1 is higher than the top tubesheet 3.

The reason why polymerization can be suppressed by setting the liquid level higher during distillation is explained as follows.

In the foregoing reboiler 2, the process liquid having reached a boiling point by distillation is further heated by the heating medium 7, thereby boiling and evaporating. Here, raising the liquid level 12 in the distillation column 1 results in applying the greater pressure to the reboiler 2 for the rise of the liquid level in the distillation column 1. Therefore, raising the liquid level 12 in the distillation column 1 causes the pressure to change, thereby raising the boiling point, though slightly. As a result, the vaporization in the reboiler 2 is suppressed, and so is polymerization.

Here, as shown in FIG. 1, let a region where the boiling (vaporization) of the process liquid occurs in the reboiler tubes 6 of the reboiler 2 be a vaporization zone 6a, while let the other region therein be a sensible heating zone 6b, and a degree of polymerization varies with a proportion of the vaporization zone 6a therein. In other words, since the compound treated in the present invention is a polymerizable compound, polymerization easily occurs in the vaporization zone. This is because, in the case where a polymerizable compound is treated, even with a polymerization inhibitor added to the compound, the polymerization inhibitor is separated therefrom when the polymerizable compound evaporates due to heating.

Therefore, in the case where the liquid level 12 in the distillation column 1 is set higher than the top tubesheet 3, the vaporization zone 6a is shorter as compared with the case where the liquid level 12 is as high as the top tubesheet 3. Therefore, polymerization is suppressed, and the heating of the process liquid can be efficiently carried out. Incidentally, the rise of the boiling point is very short, since the height of the liquid level 12 is set in a range of 0.1 to 0.8 time the value of L according to the outlet nozzle inside diameter (D1), but it exhibits an extremely remarkable effect from viewpoint of suppression of polymerization. The vaporization zone 6a is preferably made as small as possible in a range such that the heat transfer coefficient does not lower. In the case where the foregoing setting is executed, hydraulic hammer does not occur, and moreover, the heat transfer coefficient hardly lowers.

Thus, the vaporization zone 6a is determined in accordance with the pressure. Since the distillation column 1 normally has a constant pressure, as the pressure at the column bottom is determined, the pressure decreases for the resistance applied to the distillation device in accordance with the quantity of the process liquid passing the tubes, that is, the size of the reboiler 2, and the position at which the liquid reaches the boiling point is determined in accordance with the decrease in the pressure. Therefore, the proportion of the vaporization zone 6a can be controlled by controlling the size of the tubes, that is, the reboiler shell inside diameter (D2), as well as the diameter (inside diameter) and length of each reboiler tube 6. Consequently, for control of pressure, it is very effective to adequately determine dimensions of the inlet-side part and outlet-side part of the reboiler 2, particularly, as described above, the dimension of the outlet-side part in which flow is in two phases of liquid and vapor and hence which greatly influences pressure.

A diameter of the reboiler tube 6 (D3: inside diameter), though more or less depending on the reboiler shell inside diameter (D2), is preferably in a range of 20 mm to 50 mm, more preferably in a range of 25 mm to 45 mm, and particularly preferably in a range of 30 mm to 40 mm. A diameter of the reboiler tube 6 (D3) that is smaller than 20 mm tends to cause formation of a polymer in the reboiler tube 6 due to narrowness of the tube. On the other hand, a diameter of the reboiler 6 (D3) that exceeds 50 mm is not preferable, since in this case the heat transfer efficiency tends to lower.

Moreover, a length of the reboiler tube 6 (D4) is preferably set so as to satisfy:

$$D4=(2 \text{ to } 20) \times D2$$

more preferably, $$D4=(2.5 \text{ to } 15) \times D2$$

or particularly preferably, $$D4=(3 \text{ to } 10) \times D2$$

If the length of the reboiler tube 6 (D4) is shorter than 2×D2, the number of reboiler tubes 6 required increases, resulting in that the reboiler shell inside diameter (D2) increases. In the case where the reboiler shell inside diameter (D2) is too great relative to an inside diameter of a reboiler tube on an inlet-side thereof (D5: hereinafter referred to as reboiler inlet nozzle inside diameter), channeling occurs, thereby making the natural circulation difficult. As a result, the operation of the distillation device tends to become unstable. On the other hand, if the length of the reboiler tube 6 (D4) is longer than 20×D2, pressure loss increases and vaporization occurs thereby causing a polymer to be formed. Incidentally, the length of the reboiler tube 6 (D4) is substantially equal to a distance from the upper surface 3a of the top tubesheet 3 to a lower surface 11a of a bottom tubesheet 11 in the reboiler 2.

Furthermore, the reboiler inlet nozzle inside diameter (D5) is preferably set so as to satisfy:

$$D5=(0.2 \text{ to } 1) \times D2$$

more preferably, $$D5=(0.3 \text{ to } 1) \times D2$$

or particularly preferably, $$D5=(0.5 \text{ to } 1) \times D2$$

In the present invention, the conduit 8 connected with the reboiler lower end 14 thereby serving as an inlet of the reboiler 2 is designed so as to have an inside diameter equal to an inside diameter of an opening 10 in the distillation column 1 for connection of the conduit 8 with a liquid-phase section of the distillation column 1. In other words, the reboiler inlet nozzle inside diameter (D5) in the present invention is equal to the opening 10 in the distillation column 1 for connection of the conduit 8 with the liquid-phase section of the distillation column 1.

Since flow is in two phases of liquid and vapor mixed in the outlet-side part of the reboiler 2 while it is in the liquid phase in the inlet-side part of the reboiler 2, pressure drop less adversely affect in the inlet-side part of the reboiler 2 than in the outlet-side part thereof. However, the liquid discharge piping 9 to deliver outside the system is provided on the inlet side of the reboiler 2. Therefore, the reboiler inlet nozzle inside diameter (D5) should be designed so that circulation disorder may not occur.

If the reboiler inlet nozzle inside diameter (D5) is less than 0.2×D2, pressure loss becomes too great, thereby resulting in that the operation of the distillation device tends to be easily affected by the liquid discharge piping 9, and hence, unstable. Besides, since the reboiler shell inside diameter (D2) is too greater than the inlet nozzle inside diameter (D5), to achieve uniform distribution of the liquid into the reboiler tubes 6 becomes difficult, and channeling occurs. On the other hand, if the reboiler inlet nozzle inside diameter (D5) exceeds 1×D2, channeling tends to occur, and formation of a polymer tends to occur where the velocity is low.

As described above, according to the method of the present invention, in distillation of a polymerizable compound or a liquid containing a polymerizable compound by using the distillation column 1 equipped with the reboiler 2 as a vertical multi-tube reboiler of a natural circulation type, for suppression of polymerization of a polymerizable compound, an outlet of an outlet nozzle 4 of the reboiler 2 to a gas-phase section of the distillation column 1 is provided at a position in accordance with an inside diameter (D1) of the outlet nozzle 4 of the reboiler 2, and a height of a liquid level 12 in the distillation column 1 is maintained lower than a lower end of an outlet of the outlet nozzle 4 to the distillation column 1 and higher than a top tubesheet 3 of the reboiler 2, so that a boiling point of a process liquid in the reboiler 2, that is, the polymerizable compound or a liquid containing the polymerizable compound, is raised. By so doing, a proportion of the vaporization zone 6a in the reboiler tube 6 is controlled. The outlet nozzle inside diameter (D1) of the reboiler 2 is set depending on the reboiler shell inside diameter (D2) of the reboiler 2.

According to the method of the present invention, formation of a polymer in the reboiler tubes 6 is effectively controlled without lowering a heat transfer efficiency in the reboiler 2, by conducting the foregoing distillation under conditions in which the foregoing D1/D2, L/D1, and H/L are set in ranges of 0.2 to 1, 0.4 to 3, and 0.1 to 0.8, respectively, or preferably in ranges of 0.3 to 1, 0.7 to 2.5, and 0.2 to 0.7, respectively, or more preferably, in ranges of 0.5 to 1, 1 to 2, and 0.3 to 0.5, respectively.

Furthermore, in this case, each reboiler tube 6 is designed so that the foregoing D3 and D4/D2 are preferably in ranges of 20 mm to 50 mm and 2 to 20, respectively, or more preferably in ranges of 25 mm to 45 mm and 2.5 to 15, respectively, or particularly preferably in ranges of 30 mm to 40 mm and 3 to 10, respectively. This arrangement is preferable with view to effectively preventing formation of a polymer in the reboiler tubes 6 without lowering a heat transfer efficiency in the reboiler 2.

Furthermore, adequately determining not only the dimension of the outlet of the reboiler 2 but also that of the inlet thereof, that is, the reboiler inlet nozzle inside diameter (D5), is extremely effective in controlling the pressure. Herein, by using a distillation column designed so that D5/D2 is preferably in a range of 0.2 to 1, more preferably in a range of 0.3 to 1, or particularly preferably in a range of 0.5 to 1, formation of a polymer in the reboiler tubes 6 can be more efficiently prevented, without lowering the heat transfer efficiency in the reboiler 2.

Figure 3:
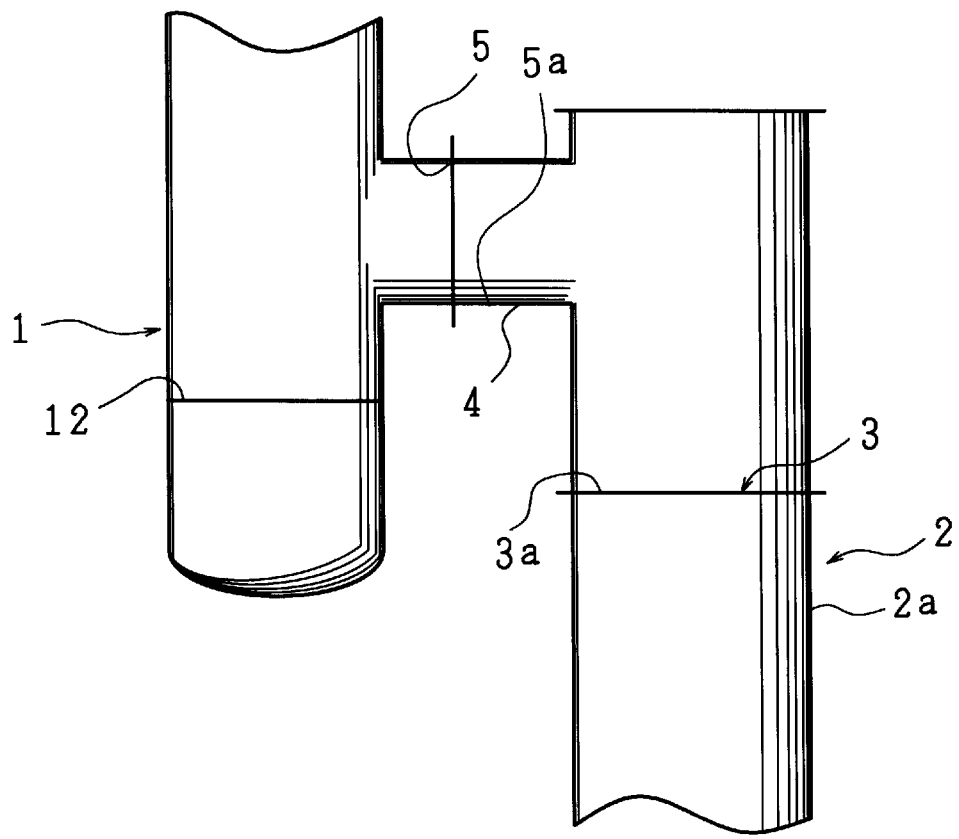
FIG. 3 is a view schematically illustrating an arrangement of another reboiler.
Figure 4:
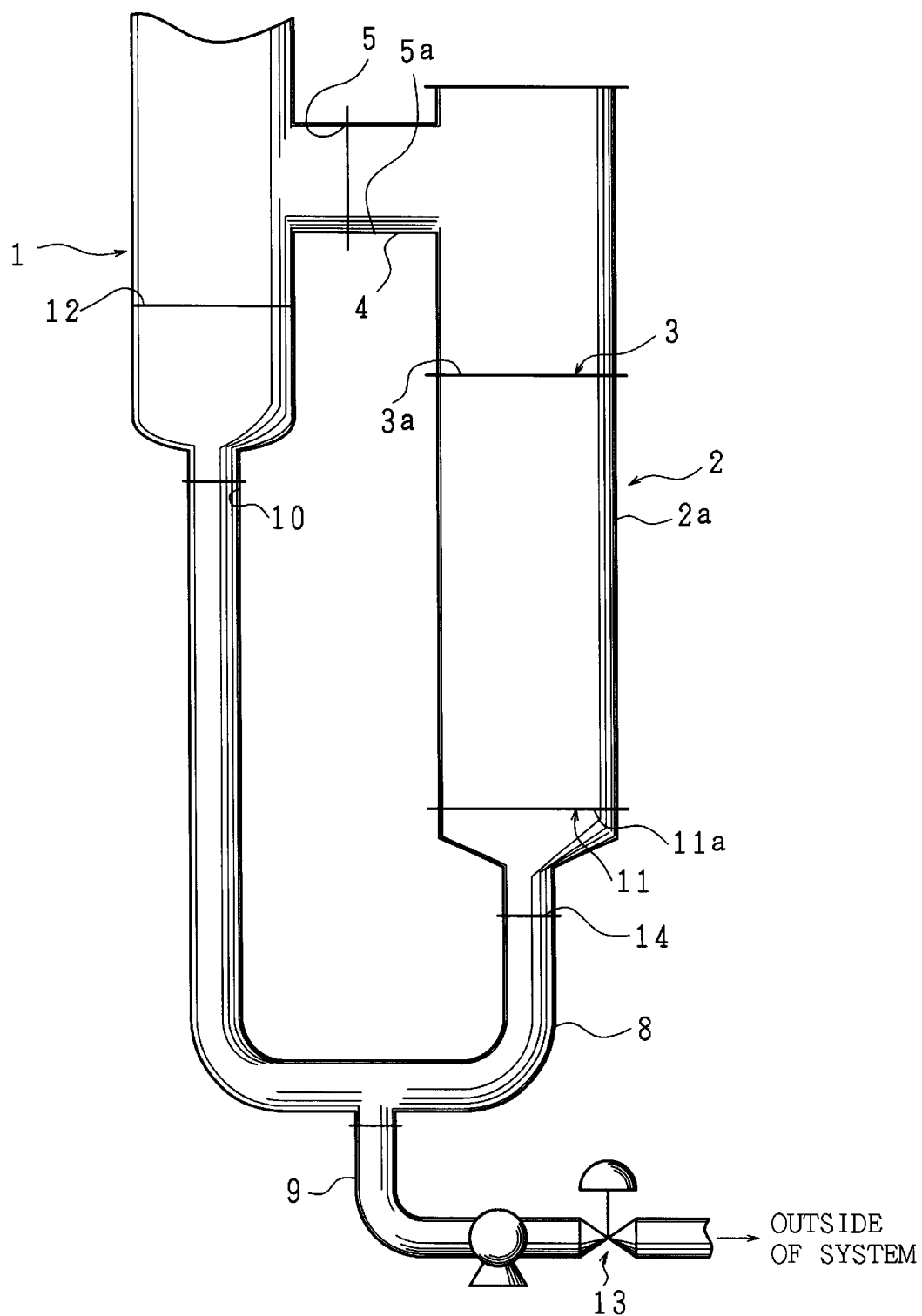
FIG. 4 is a view schematically illustrating an embodiment of a distillation device equipped with the reboiler shown in FIG. 3.

Incidentally, the shape of the reboiler outlet nozzle 4 is not limited to that shown in FIG. 1. The reboiler outlet nozzle 4 that is a straight pipe may be provided at 90° with respect to the reboiler shell 2a as shown in FIGS. 3 and 4 so as to connect the reboiler shell 2a with the distillation column 1, or it may have any other common shape. FIG. 3 is a view schematically illustrating a reboiler 2 in another shape, and FIG. 4 is a view schematically illustrating an embodiment of a distillation device equipped with the reboiler 2 shown in FIG. 3. Note that in FIG. 3 as well, a joint part of the column bottom of the distillation column 1 with the conduit 8 and the liquid discharge piping 9 is omitted for simplification of the drawing.

With view to suppression of pressure loss at the outlet part (opening 5) of the reboiler outlet nozzle 4, however, the reboiler outlet nozzle 4 preferably has a curving shape as shown in FIGS. 1 and 2.

Furthermore, in the foregoing distillation, any common polymerization inhibitor such as phenothiazine or hydroquinone is applicable. However, by applying a molecular oxygen containing gas as a polymerization inhibitor, it is possible to increase the heat transfer coefficient and to further enhance the effect of preventing fouling of the reboiler tubes 6.

The foregoing distillation method in accordance with the present invention is suitable for purification of a polymerizable compound, separation or purification of a compound to be obtained from a liquid containing a polymerizable compound.

The following description will explain the present invention in more detail, referring to examples and comparative examples, but the present invention is not limited to these. Note that "%" in the examples and comparative examples below refers to "percent by weight (wt %)". Besides, "D1", "D2", "D3", "D4", "D5", "L", and "H" respectively designate the same as those in the above descriptions. Further, a quantity of vapor used as heating medium (heating medium quantity) is set equal to each other in the examples and comparative examples below.

Example 1

A distillation column equipped with a vertical multi-tube reboiler having 600 stainless steel tubes was used as the distillation device of the present invention. An outside diameter, a wall thickness, and a length of a reboiler tube of the foregoing vertical multi-tube reboiler were 34 mm, 1.8 mm, and 4000 mm, respectively (i.e., D3=30.4 mm, D4=4000 mm). D1, D5, D2, and L were set to 1000 mm, 650 mm, 1210 mm, and 800 mm, respectively. To this distillation column, a methacrylic acid containing liquid having the following composition was supplied at a rate of 14 m$^3$/hr and distilled under a column top pressure of 140.00 hPa (105 Torr):

| | |
|---|---|
| methacrylic acid | 23% |
| acrylic acid | 0.23% |
| solvent | 75.6% |
| phenothiazine | 200 ppm |

A temperature inside the reboiler tube was 120° C., and steam of 0.588 MPaG (6 Kg/cm$^2$G) was supplied at a rate of about 2000 kg/hr. Incidentally, the heating medium (steam) quantity was controlled with use of a control valve. Therefore, pressure drop occurs, and a difference is produced between the pressure at the reboiler inlet (reboiler shell side pressure) and the heating medium supply pressure. In the present example, due to pressure drop caused by the control valve, the pressure consequently lowered at the reboiler inlet to 0.196 MPaG (2.0 Kg/cm$^2$G), and thereafter steam was supplied under the same pressure.

From the bottom of the distillation column, methacrylic acid containing bottoms having the following composition were obtained at a rate of 2.4 m$^3$/hr:

| | |
|---|---|
| methacrylic acid | 99.6% |
| acrylic acid | 50 ppm |
| phenothiazine | 1000 ppm |

In this distillation, H was 300 mm. Respective factors in this distillation, that is, distillation conditions, were as follows:

D1/D2=0.826

L/D1=0.800

H/L=0.375

D4/D2=3.306

D5/D2=0.537

During one-year operation under the above-described conditions, no rise of the heating-use steam pressure (reboiler shell side pressure) was not observed. After one-year operation under the above-described conditions, inside of every reboiler tube was checked, and there was no plugging.

Comparative Example 1

Distillation was conducted in the same manner as in Example 1 except that H=50 mm (H/L=0.063). Herein, H was changed by controlling the quantity of the bottoms discharged.

After about one month, a rise of the heating-use steam pressure (reboiler shell side pressure) was observed. After three-month operation, inside of every reboiler tube was checked, and about 100 tubes were found to be plugged with a polymer.

Comparative Example 2

Distillation was conducted in the same manner as in Example 1 except that H=650 mm (H/L=0.813). Herein, H was changed by controlling the quantity of the bottoms discharged.

After about two weeks, an increase in a quantity of a polymer in the bottoms discharge liquid, and after two months, the device became inoperable. Inside of every reboiler tube was checked, and most of the tubes were found to be plugged with the polymer.

Example 2

A distillation column equipped with a vertical multi-tube reboiler having 160 stainless steel tubes was used as the distillation device of the present invention. An outside diameter, a wall thickness, and a length of a reboiler tube of the foregoing vertical multi-tube reboiler were 34 mm, 2.0 mm, and 4000 mm, respectively (i.e., D3=30 mm, D4=4000 mm). D1, D5, and D2 were 500 mm, 300 mm, and 600 mm, respectively, while L was 900 mm. To this distillation column, a methacrylic acid containing liquid having the following composition was supplied at a rate of 2.3 m$^3$/hr and distilled under a column top pressure of 80.0 hPa (60 Torr):

| | |
|---|---|
| methacrylic acid | 50% |
| methyl methacrylate | 46% |
| hydroquinone | 0.2% |

A temperature inside the reboiler tube was 100° C., and steam of 0.588 MPaG (6 Kg/cm$^2$G) was supplied at a rate of about 1000 kg/hr. Here, a reboiler shell side pressure was 0.088 MPaG (0.9 Kg/cm$^2$G).

From the bottom of the distillation column, methacrylic acid containing bottoms having the following composition were obtained at a rate of 0.8 m$^3$/hr:

| | |
|---|---|
| methacrylic acid | 98% |
| methyl methacrylate | 1% |
| hydroquinone | 0.6% |

In this distillation, H was 300 mm. Respective factors in this distillation, that is, distillation conditions, were as follows:

D1/D2=0.833

L/D1=1.800

H/L=0.333

D4/D2=6.667

D5/D2=0.500

During one-year operation under the above-described conditions, no rise of the heating-use steam pressure (reboiler shell side pressure) was observed. After the one-year operation, inside of every reboiler tube was checked, and there was no plugging.

Example 3

A distillation column equipped with a vertical multi-tube reboiler having 270 stainless steel tubes was used as the distillation device of the present invention. An outside diameter, a wall thickness, and a length of a reboiler tube of the foregoing vertical multi-tube reboiler were 34 mm, 1.8 mm, and 4000 mm, respectively (i.e., D3=30.4 mm, D4=4000 mm). D1, D5, and D2 were 650 mm, 450 mm, and 850 mm, respectively, while L was 720 mm. To this distillation column, an acrylic acid containing liquid having the following composition was supplied at a rate of 9.4 m$^3$/hr and distilled under a column top pressure of 53.3 hPa (40 Torr):

| | |
|---|---|
| acrylic acid | 95% |
| acetic acid | 2.6% |
| phenothiazine | 200 ppm |

A temperature inside the reboiler tube was 90° C., and steam of 0.196 MPaG (2 Kg/cm$^2$G) was supplied at a rate of about 4000 kg/hr. Here, a reboiler shell side pressure was 0.137 MPaG (1.4 Kg/cm$^2$G).

From the bottom of the distillation column, acrylic acid containing bottoms having the following composition were obtained at a rate of about 8 m$^3$/hr:

| | |
|---|---|
| acrylic acid | 97% |
| acetic acid | 200 ppm |

In this distillation, H was 360 mm. Respective factors in this distillation, that is, distillation conditions, were as follows:

D1/D2=0.765
L/D1=1.108
H/L=0.500
D4/D2=4.706
D5/D2=0.529

During four-month operation under the above-described conditions, no rise of the heating-use steam pressure (reboiler shell side pressure) was observed. After the four-month operation, inside of every reboiler tube was checked, and there was no plugging.

Comparative Example 3

Distillation was conducted in the same manner as in Example 3 except that the liquid level was set as high as the top tubesheet of the reboiler (H=0 mm). Herein, H was changed by controlling the quantity of the bottoms discharged.

After about one month, a rise of the heating-use steam pressure (reboiler shell side pressure) was observed. After the three-month operation, inside of every reboiler tube was checked, and about 50 tubes were found to be plugged with a polymer.

Comparative Example 4

Distillation was conducted in the same manner as in Example 3 except that:
 a distillation column equipped with a vertical multi-tube reboiler having 270 stainless steel tubes, whose outside diameter, wall thickness, and length were 34 mm, 1.8 mm, and 4000 mm, respectively (i.e., D3=30.4 mm, D4=4000 mm), and in which D1, D5, and D2 were 650 mm, 450 mm, and 850 mm, respectively, while L was 195 mm, was used; and
 H was changed to 97 mm (H/L=0.497).

In other words, distillation was carried out by setting all the factors (distillation conditions) substantially the same as those in Example 3 except that L/D1 was changed from 1.11 to 0.3. Herein, H was changed by controlling the quantity of the bottoms discharged.

After one-month operation, inside of every reboiler tube was checked, and about 70 tubes were found to be plugged, while deposit of a polymer on the top tubesheet, that is, in the tubesheet section, was observed.

Comparative Example 5

Distillation was conducted in the same manner as in Example 3 except that:
 a distillation column equipped with a vertical multi-tube reboiler having 270 stainless steel tubes, whose outside diameter, wall thickness, and length were 34 mm, 1.8 mm, and 4000 mm, respectively (i.e., D3=30.4 mm, D4=4000 mm), and in which D1, D5, and D2 were 950 mm, 450 mm, and 850 mm, respectively, while L was 1050 mm (L/D1=1.105), was used; and
 H was changed to 525 mm (H/L=0.500).

In other words, distillation was carried out by setting all the factors (distillation conditions) substantially the same as those in Example 3 except that D1/D2 was changed from 0.765 to 1.118. Herein, H was changed by controlling the quantity of the bottoms discharged.

After one-month operation, inside of every reboiler tube was checked, and no plugging was observed in the tubes, but deposit of a polymer on the top tubesheet, that is, in the tubesheet section, was observed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for distilling a polymerizable compound or a liquid containing a polymerizable compound, wherein the polymerizable compound is at least one selected from among the group consisting of (meth)acrylic acids and esters of the same, the method comprising:
 setting a distillation column which is equipped with a vertical multi-tube reboiler having a reboiler shell forming its outer structure, wherein the reboiler is structured and arranged to have an outlet nozzle of said reboiler to a gas-phase section of said distillation column, at a position satisfying:

$$L=(0.4 \text{ to } 3) \times D1$$

where L is a distance from a top tubesheet of said reboiler to a lower end of the outlet of the nozzle, and D1 is the outlet nozzle inside diameter;
 setting an inside diameter (D1) of the outlet nozzle to 0.2 to 1 times the inside diameter (D2) of the reboiler shell;
 supplying a polymerizable compound or a liquid containing a polymerizable compound to said distillation column; and
 performing distillation of the polymerizable compound while maintaining a liquid level of said polymerizable compound or said liquid containing a polymerizable compound in said distillation column in a range satisfying:

$$H=(0.1 \text{ to } 0.8) \times L$$

where H is a height of the liquid level from the top tubesheet of said reboiler.

2. A method for distilling a polymerizable compound or a liquid containing a polymerizable compound, the method comprising:
 setting a distillation column which is equipped with a vertical multi-tube reboiler having a reboiler shell forming its outer structure, wherein the reboiler is structured and arranged to have an outlet nozzle of said reboiler to a gas-phase section of said distillation column, at a position satisfying:

$$L=(0.4 \text{ to } 3) \times D1$$

where L is a distance from a top tubesheet of said reboiler to a lower end of the outlet of the nozzle, and D1 is the outlet nozzle inside diameter;
 setting an inside diameter (D1) of the outlet nozzle to 0.2 to 1 times the inside diameter (D2) of the reboiler shell;
 supplying a polymerizable compound or a liquid containing a polymerizable compound to said distillation column; and maintaining a liquid level of said polymerizable compound or said liquid containing a polymerizable compound in said distillation column in a range satisfying:

$$H = (0.1 \text{ to } 0.8) \times L$$

where H is a height of the liquid level from the top tubesheet of said reboiler, and wherein:

said reboiler is a vertical multi-tube reboiler equipped with a plurality of reboiler tubes that have an inside diameter (D3) in a range of 20 mm to 50 mm each, and that have a length (D4) in a range of 2 to 20 times the reboiler shell inside diameter (D2) each.

3. The method as set forth in claim 1 or 2, wherein:

a reboiler inlet nozzle inside diameter (D5) of said reboiler is 0.2 to 1 times the reboiler shell inside diameter (D2).

4. The method for distilling a polymerizable compound or a liquid containing a polymerizable compound as set forth in claim 1 or 2, further comprising adjusting a quantity of discharged bottoms according to a quantity of the polymerizable compound or liquid supplied to said distillation column.

* * * * *